United States Patent [19]

Finkenzeller et al.

[11] 4,232,227

[45] Nov. 4, 1980

[54] X-RAY EXAMINATION APPARATUS

[75] Inventors: Johann Finkenzeller; Guënter Holzermer; Gerhard Wenzek, all of Erlangen, Fed. Rep. of Germany

[73] Assignee: Siemens Aktiengesellschaft, Berlin & Munich, Fed. Rep. of Germany

[21] Appl. No.: 943,069

[22] Filed: Sep. 18, 1978

[30] Foreign Application Priority Data

Sep. 30, 1977 [DE] Fed. Rep. of Germany ....... 2744139

[51] Int. Cl.$^2$ ............................................. G03B 41/16
[52] U.S. Cl. ................................. 250/468; 250/402
[58] Field of Search ............... 250/468, 471, 511, 512, 250/513, 402, 490

[56] References Cited

U.S. PATENT DOCUMENTS

| | | | |
|---|---|---|---|
| 3,764,808 | 10/1973 | Lackey et al. | 250/468 |
| 3,976,887 | 8/1976 | Holzermer et al. | 250/471 |
| 3,986,034 | 10/1976 | Wittkopp et al. | 250/468 |

FOREIGN PATENT DOCUMENTS 2257778  11/1971  Fed. Rep. of Germany .

*Primary Examiner*—Craig E. Church

*Attorney, Agent, or Firm*—Hill, Van Santen, Steadman, Chiara & Simpson

[57] ABSTRACT

The disclosure relates to an x-ray examination apparatus comprising an examination table, a patient support platform resting on the examination table, an x-ray source, a remotely directed collimator for restricting the radiation beam according to cassette size (film format), a longitudinal transport carriage movable along the length of the patient support platform, and a cassette drawer capable of insertion in the longitudinal transport carriage, with clamping jaws for the purpose of the support-mounting of an insertable x-ray film cassette. In order to render possible a free removal of the cassette drawer during fluoroscopy, in spite of the necessary transmission of the scanned cassette dimensions for the purpose of collimator adjustment during radiography, the longitudinal transport carriage carries two sensors, coupled with one mechanical-electrical transducer each, for sensing the length and width of the x-ray film cassette clamped in the inserted cassette drawer. The sensors are resiliently urged to a rest position clear of the image intensifier, while being actuated by cassette insertion to assume their respective sensing positions.

8 Claims, 2 Drawing Figures

X-RAY EXAMINATION APPARATUS

BACKGROUND OF THE INVENTION

The invention relates to an x-ray examination apparatus comprising an examination table, a patient support platform resting on the examination table, an x-ray source with a remote-controllable collimator (or diaphragm) restricting the radiation beam, a longitudinal transport carriage movable along the length of the patient support platform, and a cassette drawer insertable into the longitudinal transport carriage, with clamping jaws for the purpose of support-mounting the insertable x-ray film cassette.

From the German Offenlegungsschrift No. 22 57 778, a control installation for the restriction of the effective radiation beam of an x-ray tube is known wherein, pursuant to insertion of an x-ray film cassette into the cassette receptacle of an x-ray examination apparatus, two continuously variable transducers installed in the cassette receptacle, are adjusted upon displacement of the clamping jaws. The one of the two transducers is adjusted by the two clamping jaws measuring the width of the x-ray film cassette, and the other transducer is adjusted by the clamping jaws measuring the length of the x-ray film cassette. These two transducers are connected to a control circuit by means of which the collimator and thus also the useful radiation beam are adjusted corresponding to the scanned cassette dimensions. In the case of this control installation, it is considered disadvantageous that the cassette receptacle, due to the electric connections of the transducers, can no longer be removed during fluoroscopy. Accordingly, in the case of this x-ray examination apparatus, the cassette receptacle must be pushed out in the direction of the table length from the fluoroscopy region during fluoroscopy. The cassette receptacle remains beneath the patient support and thus obstructs the adjustability of the fluoroscopy installation in the direction of the table length.

The U.S. Pat. No. 3,986,034 discloses a cassette support drawer insertable beneath the patient support wherein one of the clamping jaws, engaging the inserted x-ray film cassette, is connected, via a lever and a cable, with a magnet which is adjustable transversely to the insert direction in the cassette drawer. The discrete positions of the magnet allocated to the different cassette dimensions are associated with reed contacts on the longitudinal transport carriage. The latter reed contacts adjust the collimator of the x-ray examination apparatus corresponding to the dimensions of the inserted x-ray film cassette. In the case of this device, the cassette drawer can, indeed, be removed from the examination table. However, it is considered disadvantageous that this device functions only in the case of specified predetermined discrete cassette dimensions. In particular, this device does not satisfy the increased safety regulations in some countries which require the correct collimation (or diaphragming-in) function in the case of random cassette dimensions and not only in the case of standardized cassette sizes.

SUMMARY OF THE INVENTION

The object underlying the invention consists in discovering a construction which permits an adjustment of the collimator in dependence upon the dimensions of an x-ray film cassette inserted into the cassette drawer. The construction should operate continuously—i.e., in the case of random, non-standardized cassette dimensions—as well as permit a free removal of the cassette drawer from the examination table unhindered by electric cables. This can become necessary in order to insert another cassette receptacle which renders possible film subdivisions, in order to insert a simultaneous cassette, or, e.g. in order to bring a sheet film changer or an image intensifier inserted beneath the examination table closer to the patient support platform.

Accordingly, in the case of an x-ray examination apparatus of the type initially cited, in accordance with the invention, there are installed, on the longitudinal transport carriage, two sensors, coupled with one mechanical-electrical transducer each, for sensing the length and width of the x-ray film cassette loaded in the inserted cassette receptacle. This construction provides the possibility of continuously measuring the cassette dimensions via the mechanical-electrical transducers as well as removing the cassette receptacle from the examination table unobstructed by the cable connections necessarily connected with the transducers. In addition, through the scanning via special sensors independent of the clamping jaws, the necessity of having two special, oppositely adjustable clamping jaw pairs is eliminated. A random centric securing of the cassette in the cassette receptacle is sufficient, such as is possible e.g. with one single clamping jaw.

The application area is significantly extended if, pursuant to the utilization of an x-ray image intensifier guided beneath the patient support platform, in an advantageous further development of the invention, the longitudinal transport carriage is provided with an opening matched to the diameter of the inlet fluorescent screen of the x-ray image intensifier. This has the advantage that the radiation path is completely free for fluoroscopy upon removal of the cassette receptacle, and that said radiation path is also not obstructed by the longitudinal transport carriage. In this manner, the otherwise necessary pushing-aside of the longitudinal transport carriage pursuant to the transition from the photography operation to the fluoroscopy operation can be dispensed with.

In a further advantageous embodiment of the invention, the longitudinal transport carriage can be constructed as a frame for the inlet fluorescent screen of the x-ray image intensifier, and can be connected with the latter. The longitudinal transport carriage hereby ceases to be a structural member which must be particularly taken into account during handling of the apparatus. Through the connection with the x-ray image intensifier, it is simultaneously ensured that the longitudinal transport carriage cannot obstruct fluoroscopy, on the one hand, and that it is always centered relative to the center of the fluoroscopy region, on the other hand. If a cassette receptacle is inserted into the longitudinal transport carriage, the latter is automatically centered (or aligned), together with the centrically clamped film cassette, relative to the preceding fluoroscopy image.

The operational reliability can be increased if the sensors are mounted in a rear corner (with respect to the insert direction) of the longitudinal transport carriage. They are thereby accommodated in an extremely protected fashion such that any actuation other than the operational actuation through the x-ray film cassette, and thus a bending (or twisting, or distortion) is virtually ruled out.

Further details of the invention shall be explained in greater detail on the basis of a sample embodiment illustrated in the accompanying sheets of drawings; and other objects, features and advantages will be apparent from this detailed disclosure and from the appended claims.

DETAILED DESCRIPTION

Figure 1:
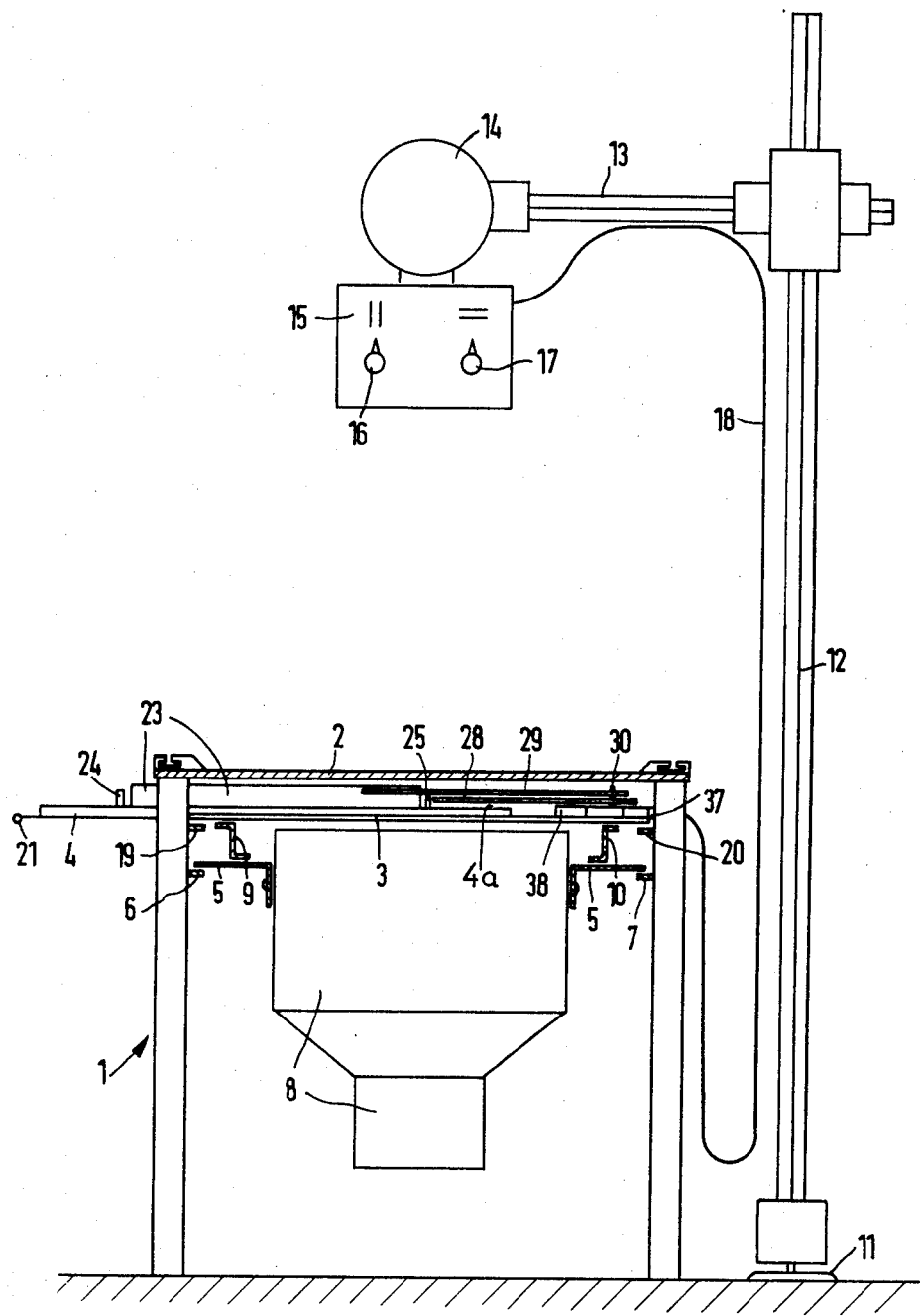
FIG. 1 illustrates an x-ray examination apparatus including a removable cassette drawer in lateral view.

In FIG. 1, an examination table 1 can be recognized comprising a patient support platform 2 and having a cassette drawer 4 providing a cassette receptacle or support beneath the patient support platform 2 which drawer is capable of insertion into a longitudinal transport carriage 3 movable in the direction of the table length. Beneath the longitudinal transport carriage 3 of the examination table 1, it is possible to recognize an image intensifier-television installation 8 mounted in a support-mounting frame 5, and capable of displacement in the direction of the table length on guide rails 6, 7. The image intensifier television installation 8 is connected via two coupling members 9, 10, to the longitudinal transport carriage 3. In addition to examination table 1, a support column 12 can be recognized which is capable of transport on the floor on a rail 11, and which bears, above the examination table 1, an x-ray tube 14 with an adjustable collimator 15, said x-ray tube 14 being connected to a horizontal extension arm 13. The collimator is manually adjustable with the aid of adjusting knobs 16, 17. These adjusting knobs are associated with remote-controllable adjusting means (not illustrated), by means of which the collimator can be adjusted electronically. For this purpose, the collimator is connected via an electric cable 18 to examination table 1.

Figure 2:
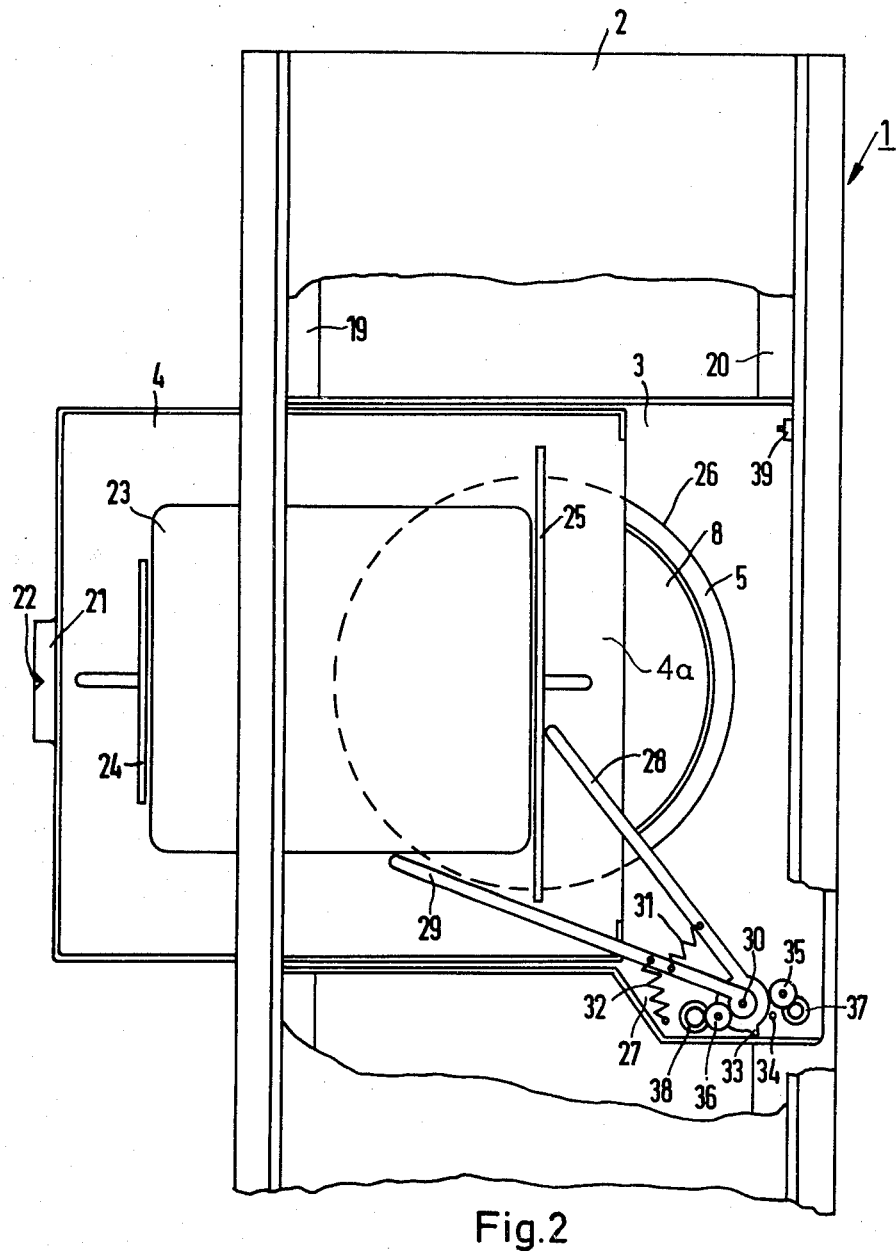
FIG. 2 illustrates a partial top plan view of the examination table of FIG. 1 with a partially inserted cassette drawer and an opened-up patient support platform.

FIG. 2 illustrates examination table 1 in a top plan view. At that location where the patient support platform 2 is opened-up, guide rails 19, 20 can be recognized along the length of which the longitudinal transport carriage 3 can be displaced. On the cassette drawer 4, provided with a handle 21 with a centering notch 22 for the light visor (or light-beam localizer, not visible) of collimator 15, an x-ray film cassette 23 is illustrated clamped between clamping jaws 24, 25. The clamping jaws 24, 25 are coupled with one another, in a manner not illustrated here, with the object of achieving a centric clamping of the x-ray film cassette 23. The longitudinal transport carriage 3 bears a central opening 26 which is matched in its diameter to the diameter of the inlet fluorescent screen of the x-ray image intensifier 8.

The longitudinal transport carriage is somewhat widened in the rear right corner (in the insert direction of drawer 4). In this widened part 27 two arm-like sensors 28, 29, each comprised of a bar with a free end, are pivotally mounted about an axis 30 orientated perpendicularly to the plane of the patient support platform 2. The sensor 28, scanning the dimension of x-ray film cassette 23 in the insert direction, is aligned as to its height above the longitudinal transport carriage 3 such that it can swing over the cassette support sheet 4a of the cassette drawer 4, but not over the rear clamping jaw 25 (projecting above the cassette support sheet 4a) for the x-ray film cassette 23. Said sensor 28 is therefore swung out of its rest position by this clamping jaw 25 pursuant to insertion of the cassette drawer 4. The other sensor 29, scanning the width (i.e., the dimension of the x-ray film cassette 23 perpendicular to the insert direction of the cassette drawer 4) is mounted above the first mentioned sensor 28 and adjusted in its height such that it can swing over the cassette support sheet 4a as well as over the rear clamping jaw 25 of the cassette drawer 4, but not over the clamped x-ray film cassette 23. The sensors are elastically interconnected by a spring 31. The sensor 29 scanning the width of the x-ray film cassette is, moreover, urged toward a rest position by an additional spring 32, in which rest position said sensor 29 itself and the other sensor 28 connected with it are removed from the fluoroscopy region. In this rest position, the sensor 28 scanning the dimension of the x-ray film cassette in the insert direction, rests with a projection 33 thereon engaging a limit stop 34 of the longitudinal transport carriage 3. Both sensors 28 and 29 have gear teeth arcuately arranged relative to the axis 30 and, via one gear wheel 35, 36, each, are coupled with one potentiometer 37, 38, each, mounted in the longitudinal transport carriage. Both potentiometers are connected via cable 18 (FIG. 1) to the control circuit of the adjustable collimator 15, so that the control circuit receives electrical information in accordance with the exact dimensions of the inserted film cassette such as 23. In addition, there is installed in the longitudinal transport carriage a limit switch 39 scanning for the complete insertion of the cassette drawer 4.

As long as no cassette drawer 4 is inserted into the longitudinal transport carriage 3, the sensor 29 for scanning the width of the x-ray film cassette is held in an outwardly-swung rest position by the spring 32, in a counterclockwise direction, out of the region of the circular opening 26 of the longitudinal transport carriage 3. At the same time, said sensor 29 also entrains, via the second spring 31, the sensor 28, for scanning the height of the x-ray film cassette in the insert direction, such a distance until its projection 33 strikes against the limit stop 34 mounted on the longitudinal transport carriage. In this position, neither of the two sensors 28, 29, projects into the fluoroscopy region. Through the coupling of the support-mounting frame 5 for the image intensifier-television installation 8 with the longitudinal transport carriage 3 it is simultaneously ensured that the circular opening 26 of the longitudinal transport carriage 3 always remains centered—even during displacement of the x-ray image intensifier 8—relative to the inlet fluorescent screen of the same.

If medical findings discovered during fluoroscopy are to be photographically recorded, it is sufficient to insert the cassette drawer 4 with an x-ray film cassette 23 clamped between the clamping jaws 24, 25, into the longitudinal transport carriage 3. As a consequence of the centering of the longitudinal transport carriage relative to the image intensifier-television installation 8, the centrically clamped x-ray film cassette 23 is simultaneously also inserted centrically relative to the fluoroscopy region. Pursuant to insertion of the cassette drawer 4, the sensor 28, scanning the dimension of the x-ray film cassette in the insert direction, initially extends over the rear edge of the cassette support sheet 4a and is pivoted in the clockwise direction by the clamping jaw 25 as shown in FIG. 2. At the same time, said sensor 28 also entrains the other sensor 29, due to the spring 31 which intercouples the two sensors 28, 29, said sensor 29 being pressed in this manner laterally against the x-ray film cassette 23. In the case of a fully inserted cassette drawer 4, both sensors 28, 29, and hence also the potentiometers 37, 38, entrained by them via the gear wheels 35, 36, occupy positions which correspond to the exact dimensions of the inserted x-ray film cassette 23. The full insertion of the cassette drawer 4 into the longitudinal transport carriage 3 and thus the switching-on of the follow-up control for the adjustable collimator 15 are controlled by the limit switch 39 mounted in the longitudinal transport carriage.

The sensor arms 28 and 29 may be intercoupled such that with an empty cassette support 4 fully inserted, the arms have an angle therebetween of about 10°. With a cassette of maximum size, the arms 28 and 29 may have an angle therebetween of about 60°.

It will be apparent that many modifications and variations may be effected without departing from the scope of the novel concepts and teachings of the present invention.

I claim as my invention:

1. An x-ray examination apparatus comprising an examination table (1), a patient support platform (2) resting on the examination table, an x-ray source with a remote-controllable collimator restricting the radiation beam, a longitudinal transport carriage (3) transportable along the length of and supported by the patient support platform, and a cassette support (4) capable of insertion into an operating position on the longitudinal transport carriage and having clamping means (24, 25) mounted thereon for positioning an insertable x-ray film cassette in fixed relation to said cassette support, said cassette support having means comprising said clamping means for providing cassette receiving regions of continuously varying size within a predetermined range, two sensor means (28, 29) being mounted on the transport carriage (3) and being operable in a sensing condition for sensing the length and width of the x-ray film cassette (23) clamped in the inserted cassette support (4), mechanical-electrical transducers (37, 38) mounted by the longitudinal transport carriage and each coupled with a respective one of said sensor means and continuously operated as a function of the mechanical position of the associated sensor means while the sensor means is in said sensing condition, and means comprising said sensor means and the mechanical-electrical transducers both mounted in the longitudinal transport carriage for enabling the complete removal of the cassette support from the longitudinal transport carriage without removing the sensor means and without removing the mechanical-electrical transducers from their mounted relationship to said longitudinal transport carriage, said sensor means having sensor positioning means (31–34) for automatically moving said sensor means to respective rest positions during removal of the cassette support from the longitudinal transport carriage, one of said sensor means (28) being positioned by said sensor positioning means so as to be displaced from its rest position in accordance with the dimension of a cassette parallel to the cassette support insert direction when the cassette support (4) with the cassette secured in said cassette receiving region is inserted into said operating position on the longitudinal transport carriage, and the other of said sensor means (29) being actuated from its rest position for sensing the transverse dimension of a cassette occupying said cassette receiving region with the displacement of the one sensor means (28) from its rest position, such cassette transverse dimension being transverse to the cassette support insertion direction in which the cassette support is inserted into said operating position on the longitudinal transport carriage.

2. An x-ray examination apparatus according to claim 1, comprising an x-ray image intensifier beneath the patient support platform, characterized in that the longitudinal transport carriage (3) is provided with an opening (26) adapted to the diameter of the inlet fluorescent screen of the x-ray image intensifier (8).

3. An x-ray examination apparatus according to claim 2, characterized in that the longitudinal transport carriage (3) is constructed in the form of a frame for the inlet fluorescent screen of the x-ray image intensifier (8) and that it is connected with the latter.

4. An x-ray examination apparatus according to claim 1, characterized in that the sensor means (28, 29) are mounted in a corner, located rearwardly with respect to an insert direction of the support (4), of the longitudinal transport carriage (3).

5. An x-ray examination apparatus according to claim 1, the longitudinal transport carriage (3) having a fluoroscopy region, characterized in that the sensor means (28, 29) in their rest positions are swung out of the fluoroscopy region.

6. An x-ray examination apparatus according to claim 1, characterized in that the two sensor means (28, 29) are provided with an arm shaped construction, and that they are swingably mounted one above the other about a common axis (30).

7. An x-ray examination apparatus according to claim 1, characterized in that said sensor positioning means comprises a spring (31), and the sensor means (28), scanning the dimension of the x-ray film cassette (23) in the insert direction of the cassette support (4), pursuant to insertion of the cassette support (4), being pressed counter to the force of said spring (31) out of its rest position by the clamping means (25) facing said sensor means (28) to actuate the other sensor means (29) toward the cassette receiving region for sensing the cassette transverse dimension.

8. An x-ray examination apparatus according to claim 1, characterized in that the two sensor means (28, 29) are elastically intercoupled at an angle of approximately 10°–60°, and that the sensor means (29), scanning the dimension of the x-ray film cassette (23) transversely to the insert direction of the cassette support (4), pursuant to the additional adjustment of the other sensor means (28) exceeding the insertion of an empty cassette support, is in turn pressed against the x-ray film cassette.

* * * * *